United States Patent
Roumeau et al.

(10) Patent No.: US 9,222,871 B2
(45) Date of Patent: Dec. 29, 2015

(54) TRACKING OF THE RATE OF CORROSION OF A METAL CONDUIT TRAVERSED BY A CORROSIVE FLUID

(75) Inventors: Xavier Roumeau, Beaumont, TX (US); Benoit Albinet, Nanterre Cedex (FR); Christophe Pelet, Angerville L'orcher (FR); Alain Houlier, Sainte Adresse (FR); Lionel Casajus-Gil, Beuzeville (FR); Guilhem Frachisse, Anglesqueville l'Esneval (FR)

(73) Assignee: TOTAL RAFFINAGE FRANCE, Puteaux (FR)

( * ) Notice: Subject to any disclaimer, the term of this patent is extended or adjusted under 35 U.S.C. 154(b) by 332 days.

(21) Appl. No.: 13/641,296

(22) PCT Filed: Apr. 18, 2011

(86) PCT No.: PCT/FR2011/050885
§ 371 (c)(1),
(2), (4) Date: May 28, 2013

(87) PCT Pub. No.: WO2011/131897
PCT Pub. Date: Oct. 27, 2011

(65) Prior Publication Data
US 2013/0236975 A1 Sep. 12, 2013

(30) Foreign Application Priority Data
Apr. 19, 2010 (FR) .................................... 10 52940

(51) Int. Cl.
*G01N 33/20* (2006.01)
*G01N 17/00* (2006.01)

(52) U.S. Cl.
CPC .............. *G01N 17/00* (2013.01); *G01N 17/006* (2013.01)

(58) Field of Classification Search
USPC ............. 422/53; 436/3, 6, 120–121, 129, 144
See application file for complete search history.

(56) References Cited

U.S. PATENT DOCUMENTS

| 3,472,632 | A | * | 10/1969 | Hervert et al. | ................. 422/242 |
| 3,479,257 | A | * | 11/1969 | Shaver | ......................... 436/144 |
| 3,567,383 | A | * | 3/1971 | Langley et al. | .................... 436/3 |
| 4,065,373 | A | * | 12/1977 | Martin et al. | .................. 204/404 |
| 4,221,651 | A | * | 9/1980 | Mansfeld et al. | ............. 204/412 |

(Continued)

FOREIGN PATENT DOCUMENTS

| GB | 2199951 | * | 7/1988 |
| GB | 2 312 279 | A | 10/1997 |

(Continued)

OTHER PUBLICATIONS

International Search Report for PCT/FR2011/050885 dated Aug. 5, 2011.

*Primary Examiner* — Arlen Soderquist
(74) *Attorney, Agent, or Firm* — Sughrue Mion, PLLC

(57) ABSTRACT

A method of tracking the rate of corrosion of a metal conduit traversed by a corrosive fluid, in which is provided a device arranged so as to form, when said device is installed on a wall of the metal conduit, a chamber able to receive gaseous hydrogen issuing by permeation across said wall of said conduit, the method comprising: (i) a step of treatment to eliminate a metallic species from the chamber, (ii) a step of measuring a quantity of hydrogen received in the chamber, with a view to estimating the rate of corrosion of the metal conduit.

8 Claims, 1 Drawing Sheet

(56) References Cited

U.S. PATENT DOCUMENTS

| | | | |
|---|---|---|---|
| 4,294,667 A * | 10/1981 | Yamamoto et al. | 205/776.5 |
| 4,416,996 A * | 11/1983 | von Klock et al. | 436/6 |
| 4,477,778 A * | 10/1984 | Lawrence | 324/466 |
| 4,718,991 A * | 1/1988 | Yamazoe et al. | 205/785.5 |
| 4,979,390 A * | 12/1990 | Schupack et al. | 73/38 |
| 5,279,169 A | 1/1994 | Freeman | |
| 5,279,795 A * | 1/1994 | Hughes et al. | 422/98 |
| 5,312,761 A * | 5/1994 | Suzuki et al. | 436/136 |
| 5,392,661 A | 2/1995 | Freeman | |
| 5,405,513 A * | 4/1995 | Lewis et al. | 205/775.5 |
| 5,858,204 A * | 1/1999 | Jambo et al. | 205/775 |
| 5,961,027 A * | 10/1999 | Szecket | 228/107 |
| 6,537,824 B1 * | 3/2003 | Correa | 436/144 |
| 6,637,253 B2 * | 10/2003 | Dean et al. | 73/23.2 |
| 6,723,566 B2 * | 4/2004 | Lee et al. | 436/144 |
| 7,687,030 B2 * | 3/2010 | Uchiyama et al. | 422/88 |
| 8,084,265 B2 * | 12/2011 | Liu et al. | 436/144 |
| 2001/0006008 A1 * | 7/2001 | Dean et al. | 73/864 |
| 2008/0148862 A1 * | 6/2008 | Aikens | 73/756 |
| 2008/0153174 A1 * | 6/2008 | Galloway et al. | 436/144 |

FOREIGN PATENT DOCUMENTS

| | | | |
|---|---|---|---|
| JP | 58-129346 A | | 8/1983 |
| JP | 61-25047 A | | 2/1986 |
| JP | 2002-289243 | * | 10/2002 |
| WO | 2008/067674 A1 | | 6/2008 |

* cited by examiner

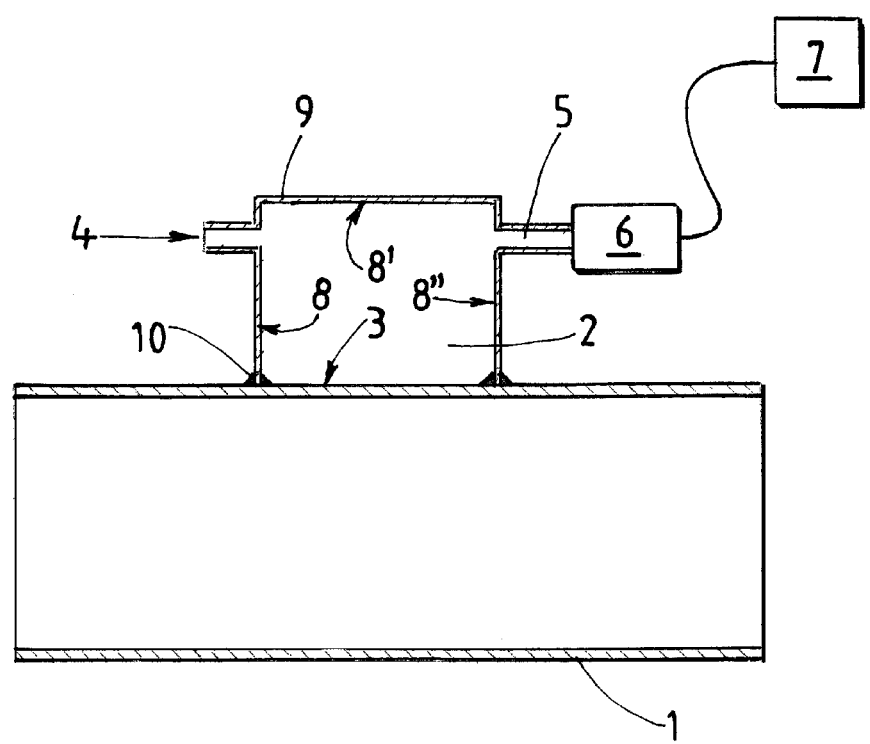

TRACKING OF THE RATE OF CORROSION OF A METAL CONDUIT TRAVERSED BY A CORROSIVE FLUID

CROSS REFERENCE TO RELATED APPLICATIONS

This application is a National Stage of International Application No. PCT/FR2011/050885 filed Apr. 18, 2011, claiming priority based on French Patent Application No. 10 52940 filed Apr. 19, 2010, the contents of all of which are incorporated herein by reference in their entirety.

The present invention relates to tracking the rate of corrosion of a metal pipe conveying a corrosive fluid, and can in particular find application in the petroleum industry.

A wall made of a ferrous metal such as carbon steel (less than 2% carbon) can corrode in the presence of acids such as $H_2S$ (hydrogen sulfide) to form ferrous sulfide (FeS) and hydrogen, and the latter can be either (i) liberated directly in the form of dihydrogen ($H_2$), or (ii) remain adsorbed on the surface of the metal in the monatomic state. Monatomic hydrogen can circulate freely through the cells of the crystal lattice and the grain boundaries of the metal, until it passes through the wall completely. In this case, two hydrogen atoms can combine to form dihydrogen and leave the wall, and diffuse into the surrounding medium, for example a gas atmosphere, a liquid or another solid.

Other acids can cause the same type of corrosion, for example naphthenic acids, which are organic acids having one or more carboxylic acid functions, which will be denoted by R—COOH. The naphthenic acids react with iron and produce hydrogen and iron naphthenates, of formula (R—COO)Fe(OOC—R') in which R and R' may be identical or different or else R and R' are joined together to form a single substituent.

Naphthenic acids occur in certain crude oils and give rise to corrosion problems in installations for petroleum storage and refining.

Naphthenic acids and hydrogen sulfide are present either alone or in combination in petroleum products, whether they are crude, semirefined (synthetic crudes) or refined.

Installations for petroleum storage and refining mainly include equipment made of alloy steel or plain steel, and are subject to strong corrosion stresses, especially when there are zones with large temperature gradients, for example in boilers, heat exchangers, distillation columns, reactors, pipelines or valves. There is external corrosion of the installations by water, oxygen of the air or other reactive species such as pollutants (sulfuric acid, $H_2S$, HCl, $NH_3$, etc.), and internal corrosion by fluids circulating in the installations, such as crude oils or liquid or gaseous refined products.

In operation, certain parts of installations for storage and refining have zones where the surface temperature of the materials can exceed 250° C. and can commonly go above 450° C. These zones are subject to severe corrosion stresses by the aforementioned acidic species and require continuous monitoring of corrosion, which can, in certain cases, amount to several millimeters of metal corroded per year. The hydrogen resulting from this corrosion can be captured by permeation through the wall of the plant. For this purpose, it is preferable to position the sensor close to the corrosion zone.

The detection and measurement of hydrogen from permeation are known in general and have resulted in the marketing of devices, some of which are based on:

collection of hydrogen by aspiration and measurement of the hydrogen pressure generated (WO 2008/067674, U.S. Pat. Nos. 5,392,661, 5,279,169);

scavenging of a surface with a gas or with air, collection of said gas or air laden with hydrogen and measurement using an electrochemical detector or by combustion (GB 2 312 279).

The detection and measurement of hydrogen resulting from permeation is a useful method for evaluating the rate of corrosion of metals, and especially of plain or alloy steels.

Commercial hydrogen sensors are described as having a working range of up to 500° C.

A measurement system was used comprising a known hydrogen sensor, assembled by pressure on a measurement zone. In tests on commercial devices, the applicant observed that measurement of hydrogen permeation varied abnormally depending on the type of metal alloy used, especially when the service temperature was above 200-250° C.

There is therefore a need for monitoring the rate of corrosion of a metal pipe conveying a corrosive fluid that is more reliable, especially in the case of relatively high temperatures.

A method is proposed for monitoring the rate of corrosion of a metal pipe conveying a corrosive fluid. A device is envisaged, arranged so as to form, when said device is installed on a wall of the metal pipe, a chamber that is able to receive gaseous hydrogen from permeation through said pipe wall. The method comprises:
  (i) a treatment step for removing, from the chamber, a metallic species that could be reduced by the gaseous hydrogen,
  (ii) a step of measuring a quantity of hydrogen received in the chamber, with a view to estimating the rate of corrosion of the metal pipe.

In particular, during the treatment step (i), at least the wall of the chamber formed by said pipe is treated on its entire surface.

A corrosive fluid can be a liquid or a gas, it can be oxidizing or reducing, acidic or basic. For example, the corrosive fluid can comprise $H_2S$ and/or a naphthenic acid. Thus, a crude oil can, depending on its composition, be a corrosive fluid in the sense of the invention.

The metallic species that could be reduced by gaseous hydrogen can comprise for example $Fe_2O_3$ (hematite), or some other.

This method makes it possible to monitor the rate of corrosion more reliably, as the values of the quantity of hydrogen measured in tests are relatively close to the expected values.

The treatment step can be carried out for example by scouring the inside surface of one or more of the chamber walls, and/or by scavenging the interior of the chamber with dihydrogen.

The scouring can be chemical, physicochemical, mechanical, or some other.

The treatment step can be carried out before installing the device on the pipe, especially in the case of mechanical scouring, carried out for example with a wire brush. For example, scouring a portion of the wall of the metal pipe can be envisaged, applying a device as described above, newly selected for example, on the scoured portion.

Alternatively, the treatment step can be carried out with the device already installed on the pipe. It can then be envisaged to treat all the internal walls of the cavity in a single operation.

Advantageously, in operation, the interior of the chamber is scavenged with an inert carrier gas, and the quantity of hydrogen contained in the carrier gas after scavenging is measured.

In the present application, "inert gas" means a gas that is free from gaseous hydrogen and, at the operating temperature, will not react with the metal pipe, or with the walls of the chamber, or with equipment for measuring the quantity of hydrogen. The inert carrier gas can for example comprise gaseous nitrogen, argon, helium and/or carbon dioxide. Air (dry or moist) is not regarded as an inert gas, in the case of metal pipes.

Reactive impurities, of the dioxygen or water vapor type, can be tolerated in the inert carrier gas, over a limited range, which can be determined empirically. For example, the inert carrier gas comprises less than 1 wt % of reactive impurities, and advantageously less than 0.1 wt %.

Preferably, however, the inert carrier gas will be free from reactive impurities, of the dioxygen or water vapor type.

Alternatively, a vacuum is created inside the chamber, and after a given time interval the pressure inside the chamber is measured, in order to estimate the quantity of gaseous hydrogen present.

The inert carrier gas can also contain hydrogen. In this case, the proportion of hydrogen in the inert carrier gas will be known, either by calibration, or by measurement before it enters the chamber. The use of a carrier gas comprising hydrogen makes it possible to detect corrosion in the system for detection and measurement, and/or lack of hermeticity. Another advantage of using a carrier gas containing hydrogen is protection of the system against corrosion.

Advantageously, the concentration of hydrogen in the inert carrier gas is between 10 and 10000 ppm. The concentration of hydrogen in the carrier gas will be adjusted as a function of the low threshold of detection of the measuring means and the maximum hydrogen concentration permitted, beyond which the measuring means become saturated.

Advantageously, the method further comprises a step of welding the device against the (external) wall of the metal pipe so as to hermetically seal the chamber. It was observed that this step leads to results that are even more reliable. Without wishing to be tied to a theory, it is not ruled out that perfect hermeticity should make it possible to prevent any escapes of hydrogen from the chamber.

Welding can be carried out with a weld bead, especially when the walls of the device are metallic. In the case of a device with walls made of polymer, it can be envisaged to use a glue that is compatible both with polymers and with metals.

Advantageously, the method further comprises a step consisting of correlating the quantity of hydrogen measured with the thickness of the corroded pipe. It is possible, for example, to use results from calibration for this purpose.

Advantageously, the method further comprises a step consisting of recording the variation in thickness of the pipe as a function of time.

Advantageously, scavenging with an inert gas is carried out before and/or during and/or after assembly.

Moreover, a system is proposed for measuring the rate of corrosion of a metal pipe comprising:
  a device arranged so as to form, when said device is installed on a wall of the metal pipe, a chamber that is able to receive gaseous hydrogen resulting from permeation through said wall of said metal pipe,
  means for measuring a quantity of hydrogen in the chamber.

The inside surfaces of the chamber walls are virtually free from metallic species that could be reduced by gaseous hydrogen.

This system can in particular be obtained after a step of removing one or more metallic species(s) that can be reduced by gaseous hydrogen.

Advantageously, the device is welded onto the wall of the metal pipe so as to hermetically seal the chamber.

Advantageously, the system further comprises:
  a gas inlet and a gas outlet connected to the chamber for scavenging said chamber with an inert carrier gas, and
  an analyzer of the quantity of hydrogen present in the gas collected at the gas outlet.

As the gas at the chamber outlet has entrained the hydrogen present in the chamber, this hydrogen is collected and the quantity collected is measured.

The gas analyzer can for example comprise a gas chromatograph, or some other.

Advantageously, the system further comprises a calculating means (or processing means) for deducing, from the measured values, the values of pipe wall thickness and optionally recording the variation of said thickness as a function of time.

This calculating means can for example comprise a processor, a CPU (Central Processing Unit), a microcontroller, a computer, or some other.

It can advantageously be envisaged to integrate the analyzer and the calculating means, and optionally the device forming a chamber, in a single piece of equipment.

Preferably, the gas analyzer comprises a detector equipped with a nickel-palladium membrane. It has been observed that detectors comprising a nickel-palladium membrane are very suitable for use in an oil refinery. These detectors are very suitable for measurement in a temperature range between −20° C. and +90° C. (inclusive). The presence of CO, $CO_2$ or $H_2S$, for concentrations below 100 ppm, does not interfere with the measurement. In the case of contamination of the detector with oxygen or by accidental exposure to the air, desorption of the membrane can be performed by means of a hydrogen-rich inert gas, for example 1% hydrogen in nitrogen or argon.

A hydrogen detector with a nickel-palladium membrane usable for the present application is marketed by the company H2Scan (Valencia, United States of America). When using an H2Scan detector, the hydrogen concentration in the inert gas will be adjusted to be between 10 ppm and 8000 ppm (inclusive). A hydrogen concentration between 50 ppm and 200 ppm (inclusive) will be particularly preferred.

The measuring means of a system according to the invention (for example an analyzer) advantageously comprise a detector comprising a nickel-palladium membrane.

The processing means of the system according to the invention are (i) connected permanently via a wire link or by radio frequency to the measuring means, or (ii) are not connected directly to said measuring means and receive the data collected by said measuring means via data transfer means, the latter being designed to be connected successively (a) to said measuring means for acquisition of the data collected by the latter, then (b) to said processing means, for retrieval of said collected data.

Moreover, an installation is proposed for storing or refining petroleum or petroleum products, comprising a system as described above.

The invention will be better understood by reference to FIG. 1, in which an example of a system according to one embodiment is shown schematically.

A pipe 1 conveys a corrosive fluid, for example petroleum.

A device 9 comprises walls 8, 8', 8" defining a cavity with an opening. The walls 8, 8" have a shape that is complementary to that of pipe 1, so that when the device 9 is welded onto the metal pipe 1, a chamber 2 is formed.

In the present application, this chamber is sometimes designated by the term "cavity" or "hermetically sealed cavity".

The hermetically sealed cavity 2 comprises a first wall 3 which is in fact a portion of the wall of metal pipe 1 for which we wish to measure a quantity of hydrogen resulting from permeation. This wall 3 is permeable to hydrogen, so that chamber 2 is able to receive the hydrogen resulting from permeation.

Device 9 comprises an inlet 4 and an outlet 5 for scavenging cavity 2 with an inert carrier gas. A flow of carrier gas can thus be established, from the inlet 4 to the outlet 5, and any dihydrogen molecules present in the chamber can thus be entrained by this flow to outlet 5.

Device 9 is arranged so as to form a closed system, so that the interior of the chamber is isolated from the ambient air.

Measuring means, for example a gas chromatograph 6, make it possible to measure a quantity of dihydrogen in the gas leaving cavity 2.

It can be envisaged to collect, for the purpose of measurement by chromatograph 6, just a proportion of the gas evacuated from chamber 2 via outlet 5, the rest of the gas evacuated from chamber 2 via outlet 5 then being entrained by means not shown in FIG. 1, as this illustration is highly schematic.

Alternatively, it can be envisaged to collect all the gas evacuated via outlet 5.

Processing means, for example a computer 7, make it possible to correlate the quantity of dihydrogen measured by chromatograph 6 and the wall thickness, notably taking into account the measurement time points.

For this purpose, computer 7 stores data obtained following calibration of equipment for measuring the quantity of hydrogen produced as a function of time, taking into account (i) the area of contact of the hermetically sealed cavity 2 with the pipe 1, (ii) the carrier gas flow rate, and (iii) the temperature.

The hermetically sealed cavity 2 of the measuring device is practically free from corrosion on its internal faces 3, 8, 8', 8".

In fact, it was observed that, in the case of metal pipes, the measured quantity of hydrogen resulting from permeation was less than the theoretical quantity, and removal of surface corrosion from the pipe that is in contact with the sealed chamber made it possible to obtain a consistent result between the theoretical and experimental quantities of hydrogen.

Metal pipes of the carbon steel type are particularly sensitive to this type of treatment.

It should be noted that once the device 9 is installed on pipe 1, the cavity is isolated from the ambient air, so that it can be expected that its internal walls 3, 8, 8', 8" will remain free from corrosion.

A weld bead 10 makes it possible to hermetically seal cavity 2, which is particularly advantageous for quantitative determination of hydrogen. In fact, hermeticity makes it possible to (i) avoid any leakage of hydrogen gas and (ii) keep the interior of chamber 2 free from any accidental oxidation that can lead to a decrease in measurement of permeated hydrogen.

To obtain this system, it can be envisaged that zone 3 of the pipe wall 1 forming part of the sealed chamber 2 undergoes treatment to remove any corrosion, prior to installation of device 9 on pipe 1. For example, a portion of the external surface of pipe 1 (including said zone 3) is rubbed with steel wool prior to application of device 9.

Once device 9 is welded on pipe 1, an additional treatment step can be envisaged, in which the sealed chamber 2 is scavenged with a stream of gaseous hydrogen.

The scavenging with a stream of gaseous hydrogen can be carried out at a relatively high temperature, for example above 250° C.

Then the sealed chamber 2 is scavenged with an inert gas, i.e. free from hydrogen and not reacting with the various parts of the system with which this gas is brought in contact. This scavenging makes it possible in particular to remove any hydrogen molecules that may be present.

Alternatively, once device 9 is welded on pipe 1, scavenging with a stream of gaseous hydrogen at high temperature is not carried out. Nevertheless, scavenging with an inert gas can be envisaged, for purging the interior of the cavity and thus evacuating the air initially present.

The invention is usable in any type of industry where there are corrosion problems, for example the petroleum, chemical, biotechnological and food industries.

The invention can be employed advantageously in the case of metal walls whose temperature is above 200° C.

In the present application, "gaseous hydrogen" means dihydrogen and the term "hydrogen" is sometimes used incorrectly to denote dihydrogen.

A metal comprises the class of metals (pure substances) and alloys thereof with one another. The metals (pure substances) and alloys can be combined with nonmetals, for example C, Si, As, P, in all proportions.

The invention claimed is:

1. A method of tracking the rate of corrosion of a metal pipe conveying a corrosive fluid,
   in which, a device installed on a wall of said metal pipe forms a chamber that is able to receive gaseous hydrogen resulting from permeation through said wall of said metal pipe,
   the method comprising:
   (i) a treatment step for removing, from the chamber, a metallic species that could be reduced by the gaseous hydrogen by scavenging the interior of said chamber with a stream comprising gaseous hydrogen, and wherein at least the chamber wall formed by said pipe is treated on its entire surface during the treatment step, and
   (ii) a step of measuring a quantity of hydrogen received in the chamber, with a view to estimating the rate of corrosion of the metal pipe.

2. The method as claimed in claim 1, further comprising:
   a step of scavenging the interior of the chamber with an inert carrier gas following the treatment step, and
   a step of measuring the quantity of hydrogen contained in the carrier gas following the scavenging step.

3. The method as claimed in claim 2, in which the inert carrier gas additionally contains hydrogen.

4. The method as claimed in claim 3, in which the hydrogen concentration in the inert carrier gas is between 10 and 10000 ppm.

5. The method as claimed in claim 1, in which the step of measuring said quantity of hydrogen received in the chamber is carried out by means of a detector comprising a nickel-palladium membrane.

6. The method as claimed in claim 1, in which the treatment step is performed by scouring the internal surfaces of at least one portion of the walls of the chamber.

7. The method as claimed in claim 1, further comprising a step of welding the device onto the wall of the metal pipe so as to hermetically seal the cavity.

8. The method as claimed in claim 1, in which the treatment step is carried out prior to installation of the device on the wall of the metal pipe.

* * * * *